(12) United States Patent
Marczyk et al.

(10) Patent No.: US 10,806,522 B2
(45) Date of Patent: Oct. 20, 2020

(54) COLPOTOMY SYSTEM FOR TOTAL LAPAROSCOPIC HYSTERECTOMY

(71) Applicant: Covidien LP, Mansfield, MA (US)

(72) Inventors: Stanislaw Marczyk, Stratford, CT (US); Anthony Calderoni, Bristol, CT (US)

(73) Assignee: Covidien LP, Mansfield, MA (US)

( * ) Notice: Subject to any disclaimer, the term of this patent is extended or adjusted under 35 U.S.C. 154(b) by 369 days.

(21) Appl. No.: 15/420,625

(22) Filed: Jan. 31, 2017

(65) Prior Publication Data

US 2017/0224421 A1 Aug. 10, 2017

Related U.S. Application Data

(60) Provisional application No. 62/293,444, filed on Feb. 10, 2016.

(51) Int. Cl.
*A61B 34/20* (2016.01)
*A61B 17/42* (2006.01)
(Continued)

(52) U.S. Cl.
CPC ...... *A61B 34/20* (2016.02); *A61B 17/320016* (2013.01); *A61B 17/4241* (2013.01);
(Continued)

(58) Field of Classification Search
CPC ..... A61B 34/20; A61B 34/70; A61B 17/4241; A61B 17/320016; A61B 2017/00123;
(Continued)

(56) References Cited

U.S. PATENT DOCUMENTS 3,877,433 A 4/1975 Librach
3,945,371 A 3/1976 Adelman
(Continued)

FOREIGN PATENT DOCUMENTS

EP 2116202 A1 11/2009
WO 2005082299 A2 9/2005
(Continued)

OTHER PUBLICATIONS

European Search Report dated Jun. 21, 2017, issued in EP Application No. 17155486.

(Continued)

*Primary Examiner* — Martin T Ton
(74) *Attorney, Agent, or Firm* — Carter, DeLuca & Farrell LLP (57) ABSTRACT

A colpotomy system includes a surgical instrument having a cutting element and a receiver at a distal end thereof and a uterine instrument. The uterine instrument has a handle operably coupled to a shaft having a balloon at a distal end thereof, the shaft extending through a retaining member to access a surgical site, the retaining member including a plurality of transmitters for transmitting at least one signal. A distance between the cutting element of the surgical instrument and one end of the retaining member of the uterine instrument is calculated to determine whether the cutting element is within a predetermined operating zone.

17 Claims, 12 Drawing Sheets

(51) Int. Cl.
  *A61B 34/00* (2016.01)
  *A61B 17/32* (2006.01)
  *A61B 18/14* (2006.01)
  *A61B 17/00* (2006.01)
  *A61B 90/00* (2016.01)
  *A61B 18/00* (2006.01)

(52) U.S. Cl.
  CPC .............. *A61B 18/14* (2013.01); *A61B 34/70* (2016.02); *A61B 2017/00123* (2013.01); *A61B 2017/00221* (2013.01); *A61B 2017/00743* (2013.01); *A61B 2017/320052* (2013.01); *A61B 2018/0063* (2013.01); *A61B 2018/00559* (2013.01); *A61B 2018/00589* (2013.01); *A61B 2018/00601* (2013.01); *A61B 2018/00607* (2013.01); *A61B 2018/1412* (2013.01); *A61B 2034/2051* (2016.02); *A61B 2090/061* (2016.02)

(58) Field of Classification Search
  CPC ........... A61B 2017/00743; A61B 2017/00221; A61B 2017/320052; A61B 2018/1412; A61B 2034/2051; A61B 2090/061; A61B 17/4216; A61B 17/4225; A61B 2018/00559; A61B 1/303; A61B 17/42
  See application file for complete search history.

(56) References Cited

U.S. PATENT DOCUMENTS

| | | |
|---|---|---|
| 3,948,270 A | 4/1976 | Hasson |
| 4,000,743 A | 1/1977 | Weaver |
| 4,022,208 A | 5/1977 | Valtchev |
| 4,337,763 A | 7/1982 | Petrassevich |
| 4,449,519 A | 5/1984 | Sarrine |
| 4,562,832 A | 1/1986 | Wilder et al. |
| 4,597,383 A | 7/1986 | VanDerBel |
| 4,901,708 A | 2/1990 | Lee |
| 5,131,380 A | 7/1992 | Heller et al. |
| 5,143,054 A | 9/1992 | Adair |
| 5,209,754 A | 5/1993 | Ahluwalia |
| 5,382,252 A | 1/1995 | Failla et al. |
| 5,394,863 A | 3/1995 | Sanford et al. |
| 5,443,058 A | 8/1995 | Ough |
| 5,445,643 A | 8/1995 | Valtchev |
| 5,464,409 A | 11/1995 | Mohajer |
| 5,487,377 A | 1/1996 | Smith et al. |
| 5,520,698 A | 5/1996 | Koh |
| 5,556,401 A | 9/1996 | Caillouette |
| 5,643,285 A | 7/1997 | Rowden et al. |
| 5,840,077 A | 11/1998 | Rowden et al. |
| 5,951,465 A | 9/1999 | Schiff et al. |
| 6,059,719 A | 5/2000 | Yamamoto et al. |
| 6,210,330 B1 | 4/2001 | Tepper |
| 6,572,631 B1 | 6/2003 | McCartney |
| 7,077,803 B2 | 7/2006 | Kasahara et al. |
| 8,603,105 B2 | 12/2013 | Sauer |
| 2001/0014805 A1 | 8/2001 | Burbank et al. |
| 2001/0021854 A1 | 9/2001 | Donnez et al. |
| 2001/0031964 A1 | 10/2001 | Gentelia et al. |
| 2001/0049509 A1 | 12/2001 | Sekine et al. |
| 2003/0109873 A1 | 6/2003 | Muzzammel |
| 2004/0116955 A1 | 6/2004 | Foltz et al. |
| 2005/0049454 A1 | 3/2005 | Ouchi |
| 2005/0080411 A1 | 4/2005 | Ouchi |
| 2005/0080412 A1 | 4/2005 | Ouchi |
| 2005/0277948 A1 | 12/2005 | Cedars et al. |
| 2005/0288660 A1 | 12/2005 | Ryan et al. |
| 2006/0027241 A1 | 2/2006 | Malecki et al. |
| 2006/0205996 A1* | 9/2006 | Presthus .............. A61B 5/1076 600/29 |
| 2007/0135819 A1 | 6/2007 | Spiritos et al. |
| 2007/0260265 A1 | 11/2007 | Walter |
| 2008/0033237 A1 | 2/2008 | Ouchi |
| 2008/0058605 A1 | 3/2008 | Sorensen |
| 2008/0097468 A1 | 4/2008 | Adams et al. |
| 2009/0131954 A1 | 5/2009 | Christian et al. |
| 2009/0209973 A1 | 8/2009 | East |
| 2009/0318950 A1 | 12/2009 | Gross |
| 2010/0106163 A1 | 4/2010 | Blair et al. |
| 2010/0145224 A1 | 6/2010 | Lee et al. |
| 2010/0305578 A1 | 12/2010 | Auerbach et al. |
| 2012/0109146 A1* | 5/2012 | Auerbach .......... A61B 17/4241 606/119 |
| 2012/0143209 A1 | 6/2012 | Brecheen et al. |
| 2012/0323079 A1 | 12/2012 | Bakare et al. |
| 2015/0351621 A1* | 12/2015 | Hill ....................... A61B 1/303 600/249 |
| 2016/0213430 A1* | 7/2016 | Mucha ................... A61B 5/062 |

FOREIGN PATENT DOCUMENTS

| | | |
|---|---|---|
| WO | 2010151429 A2 | 12/2010 |
| WO | 2015138708 A1 | 9/2015 |

OTHER PUBLICATIONS

European Examination Report dated Mar. 13, 2019, issued in EP Appln. No. 17 155 486.

* cited by examiner

COLPOTOMY SYSTEM FOR TOTAL LAPAROSCOPIC HYSTERECTOMY

CROSS-REFERENCE TO RELATED APPLICATIONS

This application claims the benefit of and priority to U.S. Provisional Patent Application No. 62/293,444 filed Feb. 10, 2016, the entire disclosure of which is incorporated by reference herein.

TECHNICAL FIELD

The present disclosure relates to medical instrumentation. More particularly, the present disclosure relates to a colpotomy system including a navigation system for determining a distance between two surgical instruments.

BACKGROUND OF RELATED ART

A uterine manipulator is used by practitioners for many laparoscopic procedures involving the female pelvic organs (e.g., uterus, tubes, ovaries, etc.) as surgery without a uterine manipulator may be more time consuming. For example, laparoscopies in which a uterine manipulator has substantial utility include tubal ligations, diagnostic laparoscopies for evaluating pelvic pain and infertility, treatment of endometriosis, removal of pelvic scars (adhesions) involving the uterus, fallopian tubes and ovaries, etc.

Most state of the art manipulators are semi-rigid instruments having a manipulating handle that is grasped outside the vagina and a working end which operatively engages tissue in the uterus. Exposure of the vital regions of the pelvis is difficult and surgery with open or laparoscopic instruments is often difficult and, in some cases, suboptimal. For example, the uterus typically can only be safely elevated about 45 degrees from the vaginal axis, or lowered 10-15 degrees from the same and movement to the right or left is minimal, at most, due to the pelvic bones. Once the uterine organ is repositioned into a desired location, the surgeon can perform one of the above mentioned surgical procedures.

One potential complication of any surgical procedure involving the uterus, e.g., partial or complete hysterectomy, is the risk of persistent and excessive bleeding due to the large blood supply in the pelvic region and blood-laden organs. For example, the open technique carries increased risk of hemorrhage due to the need to move the intestinal organs and bladder in order to reach the reproductive organs and to search for collateral damage from endometriosis or cancer. However, an open hysterectomy provides the most effective way to ensure complete removal of the reproductive system, as well as providing a wide opening for visual inspection of the abdominal cavity.

Some hysterectomies are done through the manipulation of the cervix and/or uterus utilizing a uterine manipulator and resection of the cervix (total hysterectomy) or uterus (supracervical) utilizing one or more laparoscopic instruments inserted through the navel (or other body access made with a trocar). Even though these techniques tend to reduce the recovery time in most instances, the risk of bleeding still remains.

SUMMARY

The present disclosure relates to a uterine instrument including a first handle portion, a second handle portion, a first shaft operably coupled to the first handle portion, the first shaft having a first balloon positioned at a distal end thereof, and a second shaft operably coupled to the second handle portion, the second shaft having a second balloon positioned at a distal end thereof. The uterine instrument further includes a retaining member configured to engage the second balloon of the second shaft, the first shaft configured to extend through the second shaft and the retaining member to access a surgical site. The retaining member includes a plurality of transmitters for transmitting at least one signal.

In disclosed embodiments, the first handle portion is a movable handle and the second handle portion is a stationary handle.

In disclosed embodiments, in operation, the first balloon is inflated to retain the first shaft in a uterus and the second balloon is inflated to seal an abdominal cavity.

In disclosed embodiments, the retaining member is a colpotomy cup.

In disclosed embodiments, the retaining member has a proximal ring and a distal ring, the proximal ring having a plurality of posts for supporting the distal ring. A transmitter of the plurality of transmitters is incorporated within the distal ring.

In disclosed embodiments, the at least one signal is a single frequency sound wave or radio wave or electromagnetic wave.

In disclosed embodiments, the uterine instrument is operated in tandem with a surgical instrument having at least one receiver for receiving the at least one signal emitted from the plurality of transmitters. The receiver is positioned at a distal end of the surgical instrument, the distal end further including a cutting element.

In disclosed embodiments, a distance between the cutting element of the surgical instrument and a distal ring of the retaining member is calculated by a processor.

In disclosed embodiments, if the distance exceeds a predetermined threshold, a notification is relayed to a user of the uterine instrument. Alternatively, if the distance exceeds a predetermined threshold, the cutting element is automatically deactivated.

The present disclosure relates to a colpotomy system including a surgical instrument having a cutting element and a receiver at a distal end thereof and a uterine instrument. The uterine instrument has a handle operably coupled to a shaft having a balloon at a distal end thereof, the shaft extending through a retaining member to access a surgical site, the retaining member including a plurality of transmitters for transmitting at least one signal. A distance between the cutting element of the surgical instrument and one end of the retaining member of the uterine instrument is calculated to determine whether the cutting element is within a predetermined operating zone.

The present disclosure further relates to a method of accessing a surgical site. The method includes introducing at the surgical site a surgical instrument having a cutting element and a receiver at a distal end thereof and introducing at the surgical site a uterine instrument having a handle operably coupled to a shaft having a balloon at a distal end thereof, the shaft extending through a retaining member to access a surgical site, the retaining member including a plurality of transmitters for transmitting at least one signal. The method further includes calculating a distance between the cutting element of the surgical instrument and one end of the retaining member of the uterine instrument and determining whether the cutting element is within a predetermined operating zone.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user.

Reference will now be made in detail to embodiments of the present disclosure. While certain exemplary embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Figure 1:
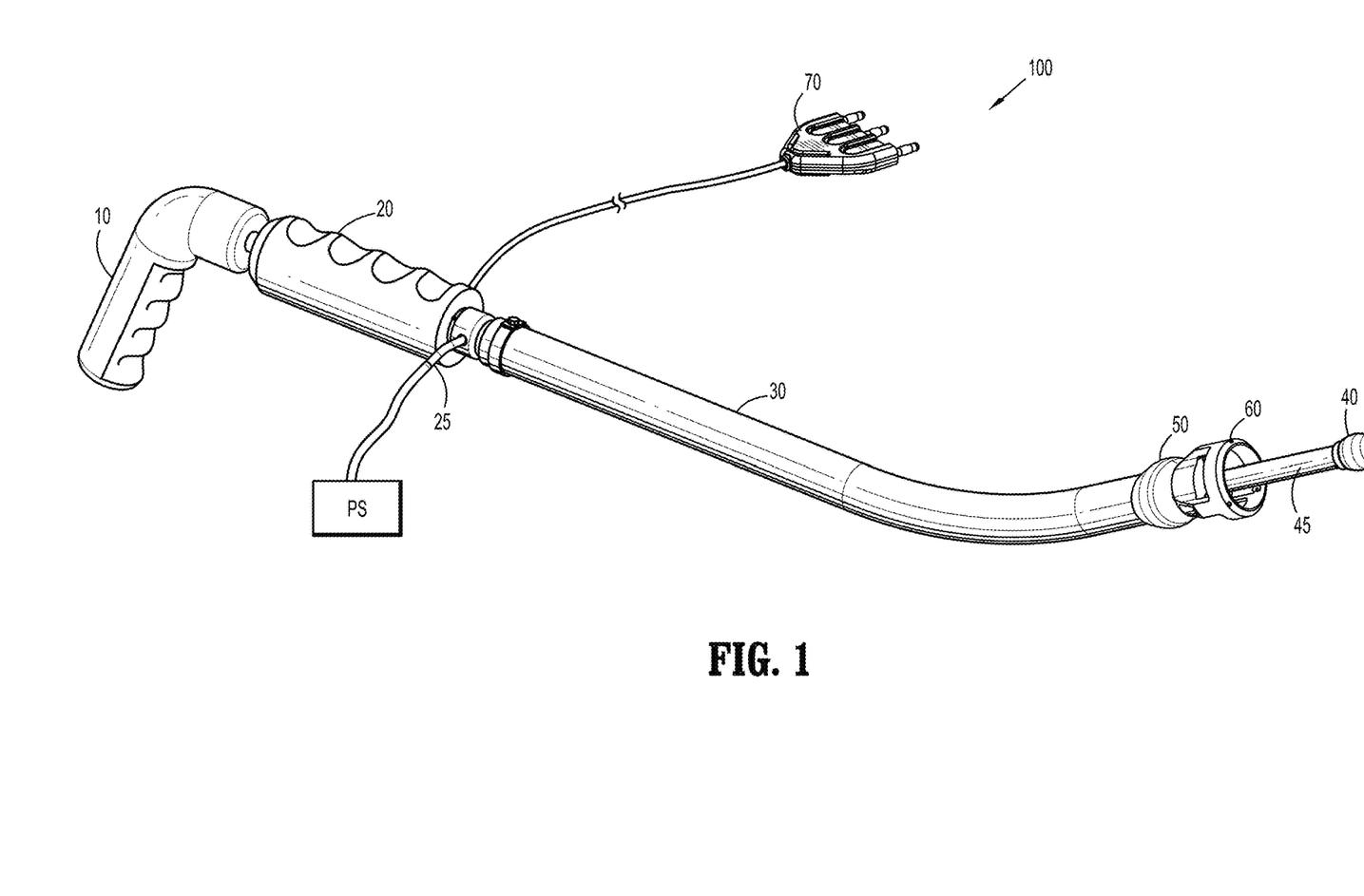
FIG. 1 is a schematic representation of a uterine manipulator, in accordance with the embodiments of the present disclosure.

FIG. 1 is a schematic representation of a uterine manipulator 100, in accordance with the embodiments of the present disclosure.

The uterine manipulator 100 includes a first handle portion 10 and a second handle portion 20. The first handle portion 10 is a movable handle and the second handle portion 20 is a stationary handle. Thus, the first handle portion 10 is movable relative to the second handle portion 20. A first shaft 45 is operably coupled to the first handle portion 10. The first shaft 45 has a first balloon 40 positioned at a distal end thereof. A second shaft 30 is operably coupled to the second handle portion 20. The second shaft 30 has a second balloon 50 positioned at a distal end thereof. The first shaft 45 and the second shaft 30 may also be rotatable. A tube 25 with a coupling provides a fluid pathway to inflate either or both of first and second balloons 40, 50. The first and second balloons 40, 50 may also be independently inflatable and each balloon 40, 50 would have a separate tube attachable to a source of inflation fluid. A pressure source "PS" may be coupled to the tube 25 and provide inflation fluid under pressure to one or both balloons 40, 50. The inflation fluid may be a liquid (e.g., sterile saline) or a gas (e.g., $CO_2$).

A retaining member 60 is configured to engage the second balloon 50 of the second shaft 30. The retaining member 60 may be a colpotomy cup. The retaining member 60 may be connected to a control box or generator (not shown) via the cable 70. The first shaft 45 is configured to extend through the second shaft 30 and through the retaining member 60 to access a surgical site, as described below with reference to FIG. 2. The retaining member 60 may be a single use component of the uterine manipulator 100.

Figure 2:
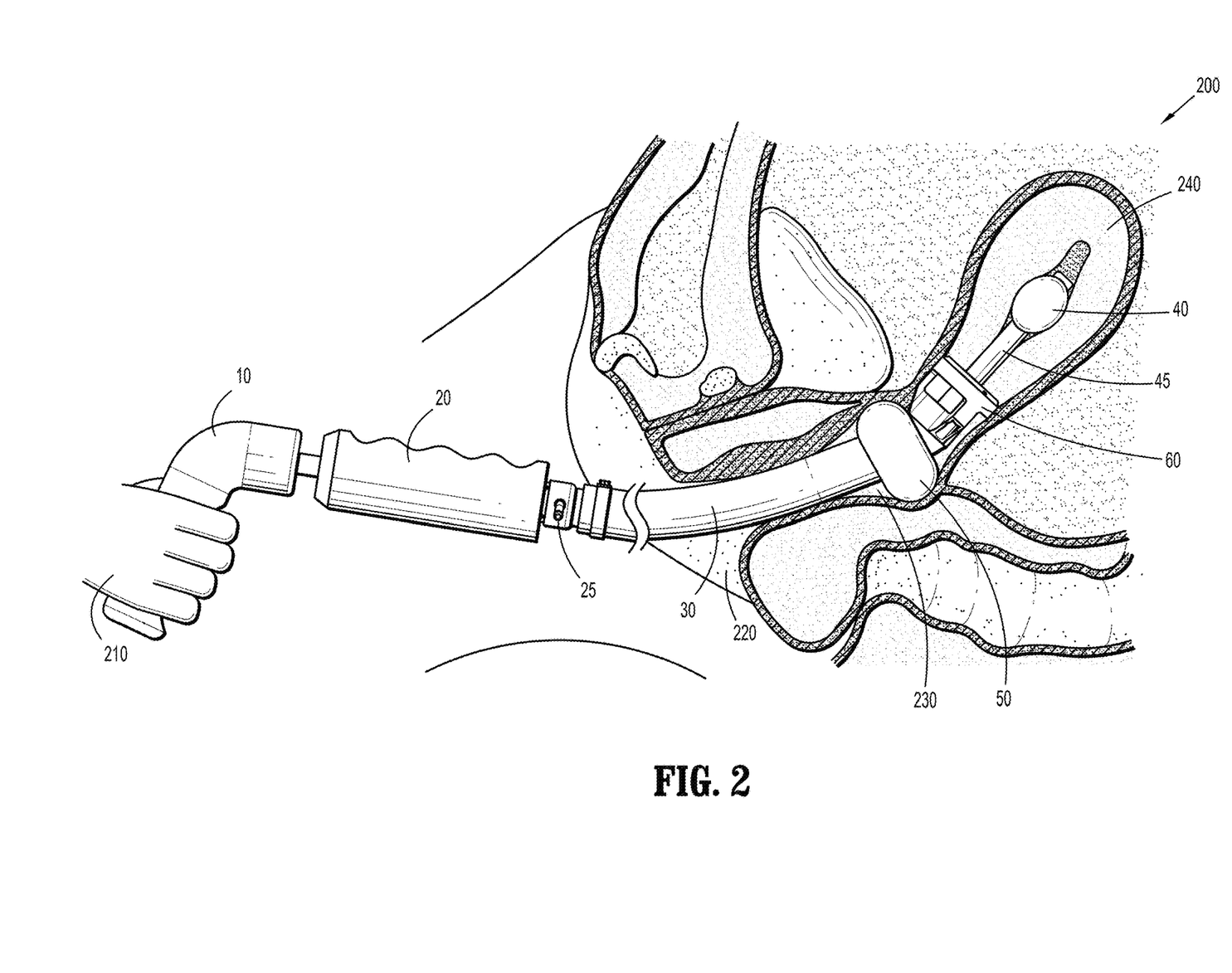
FIG. 2 illustrates the uterine manipulator of FIG. 1 entering and being retained within the uterus, in accordance with the embodiments of the present disclosure.

FIG. 2 illustrates the uterine manipulator 100 of FIG. 1 entering and being retained within a uterus 200, in accordance with the embodiments of the present disclosure.

In operation, a distal end of the uterine manipulator 100 enters the opening 220 of the uterus 200. The first balloon 40 is inflated within the cervical cavity 240 and the second balloon 50 is inflated within the vaginal cavity 230. Thus, the first balloon 40 is inflated to retain the first shaft 45 in the uterus 200 and the second balloon 50 is inflated to seal an abdominal cavity and provide a substantially fluid-tight barrier.

Figure 3:
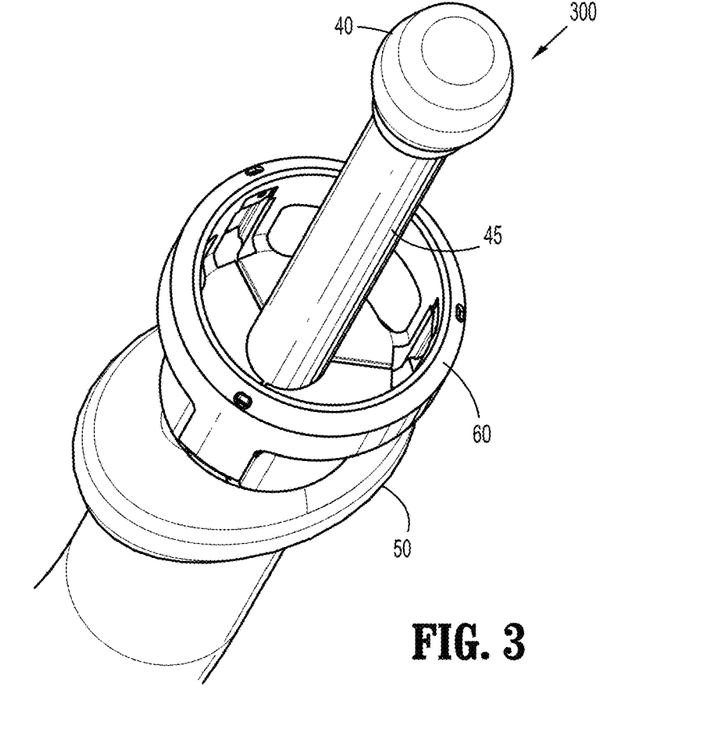
FIG. 3 illustrates an enlarged view of the distal end of the uterine manipulator of FIG. 1, in accordance with the embodiments of the present disclosure.

FIG. 3 illustrates an enlarged view 300 of the distal end of the uterine manipulator 100 of FIG. 1, in accordance with the embodiments of the present disclosure.

The enlarged view 300 illustrates the first shaft 45 extending through a central opening 450 (see FIG. 4) of the retaining member 60. First and second balloons 40, 50 are shown in a deflated state.

Figure 4:
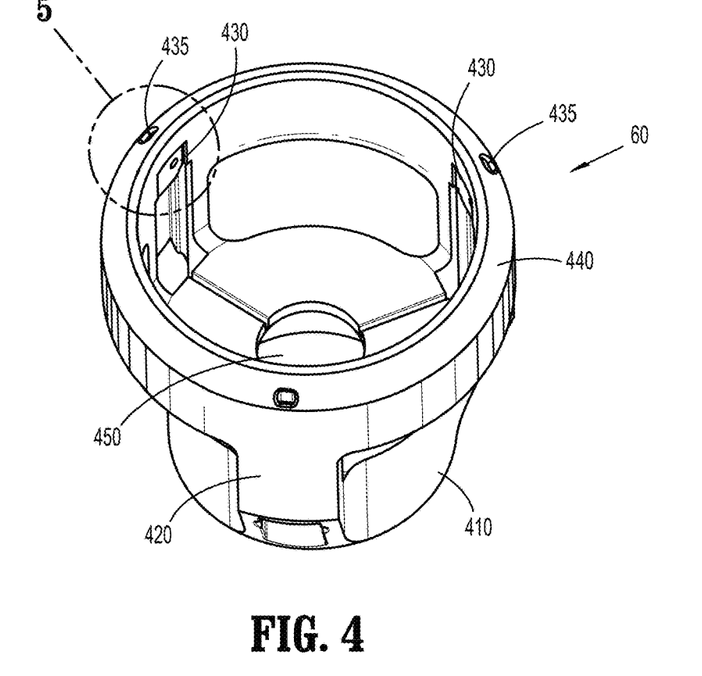
FIG. 4 illustrates the retaining member of the uterine manipulator of FIG. 1, in accordance with the embodiments of the present disclosure.

FIG. 4 illustrates the retaining member 60 of the uterine manipulator 100 of FIG. 1, in accordance with the embodiments of the present disclosure.

The retaining member 60 includes a proximal ring 410 and a distal ring 440. The proximal ring 410 has a plurality of posts 420 for supporting the distal ring 440. In one exemplary embodiment, there are three posts 420. The retaining member 60 further includes a central opening 450 for receiving the first shaft 45, as discussed above with reference to FIG. 3. Alternatively, the proximal ring 410 may be a solid ring with no posts.

The distal ring 440 includes a plurality of transmitters 430. In the exemplary embodiments there are 3 transmitters 430 embedded or incorporated within the distal ring 440. Each transmitter 430 may be aligned with a post 420. Each transmitter 430 may emit a single frequency sound wave through a respective opening 435. Of course, one skilled in the art may contemplate the transmitters 430 transmitting other types of signals, such as electromagnetic signals or radio signals. The transmitters 430 may emit the same frequency or each transmitter 430 may emit a unique frequency.

Figure 5:
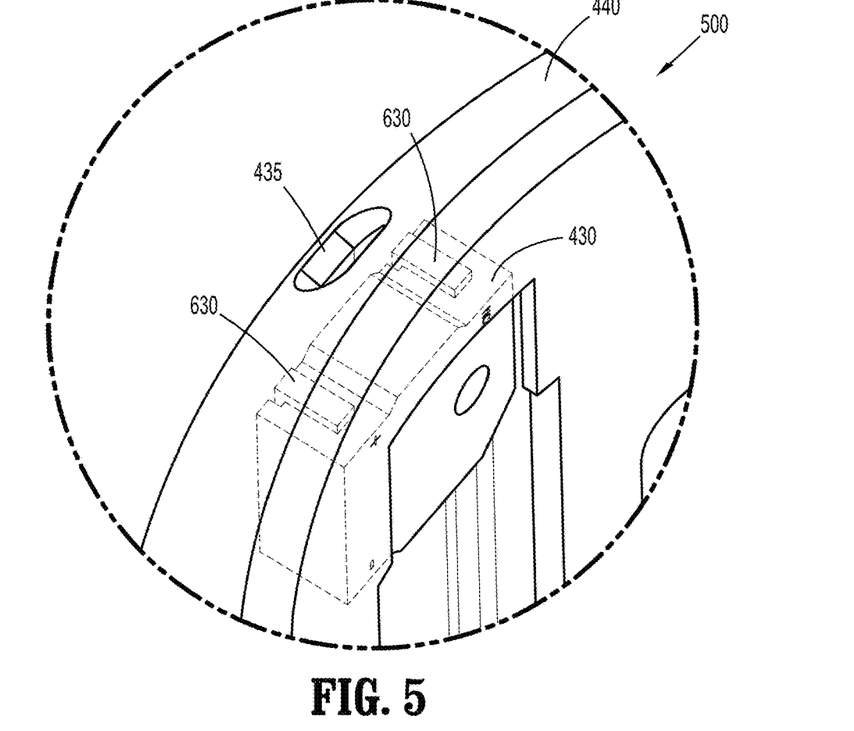
FIG. 5 illustrates the area of detail of FIG. 4 showing a transmitter embedded within the retaining member of the uterine manipulator of FIG. 1, in accordance with the embodiments of the present disclosure.
Figure 6:
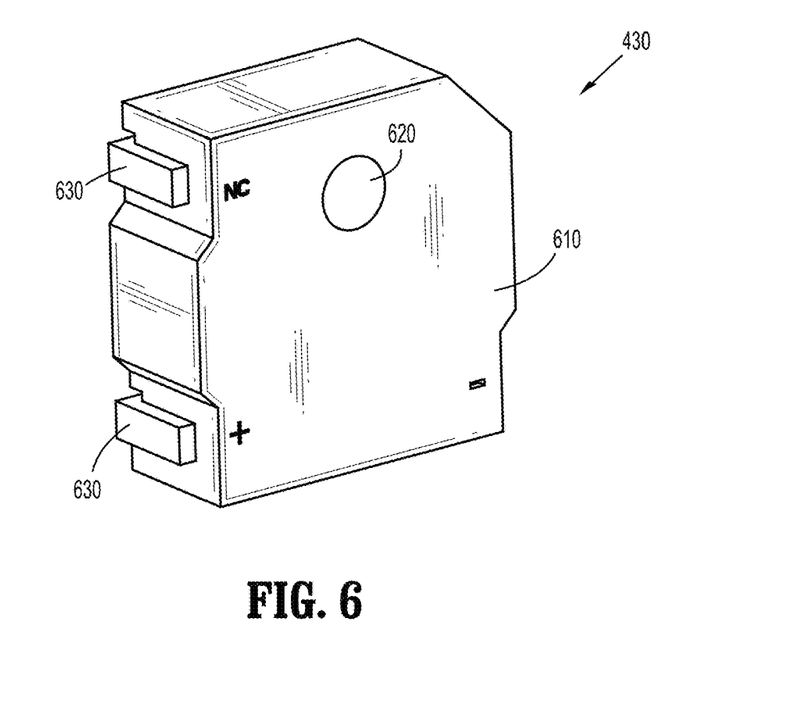
FIG. 6 illustrates the transmitter of FIG. 5, in accordance with the embodiments of the present disclosure.

FIG. 5 is an enlarged view 500 illustrating the area of detail of FIG. 4 showing a transmitter 430 embedded or incorporated within the retaining member 60 of the uterine manipulator 100 of FIG. 1, in accordance with the embodiments of the present disclosure, whereas FIG. 6 illustrates the transmitter 430 of FIG. 5, in accordance with the embodiments of the present disclosure.

The transmitter 430 has a body portion 610 with a pair of electrical contacts 630, as well as a speaker 620. The pair of electrical contacts 630 are used to supply power to generate, for example, the sound wave that is emitted through speaker 620. Of course, one skilled in the art may contemplate the transmitters 430 transmitting other types of signals, such as electromagnetic signals or radio signals. The transmitter 430 is aligned with the opening 435 of the distal ring 440. The transmitter 430 is also aligned with the posts 420 of the retaining member 60. Even though the exemplary embodiments refer to three transmitters 430, one skilled in the art may contemplate any number of transmitters 430 embedded or incorporated within the distal ring 440 or any other portion or portions of the retaining member 60.

Figures 7, 8:
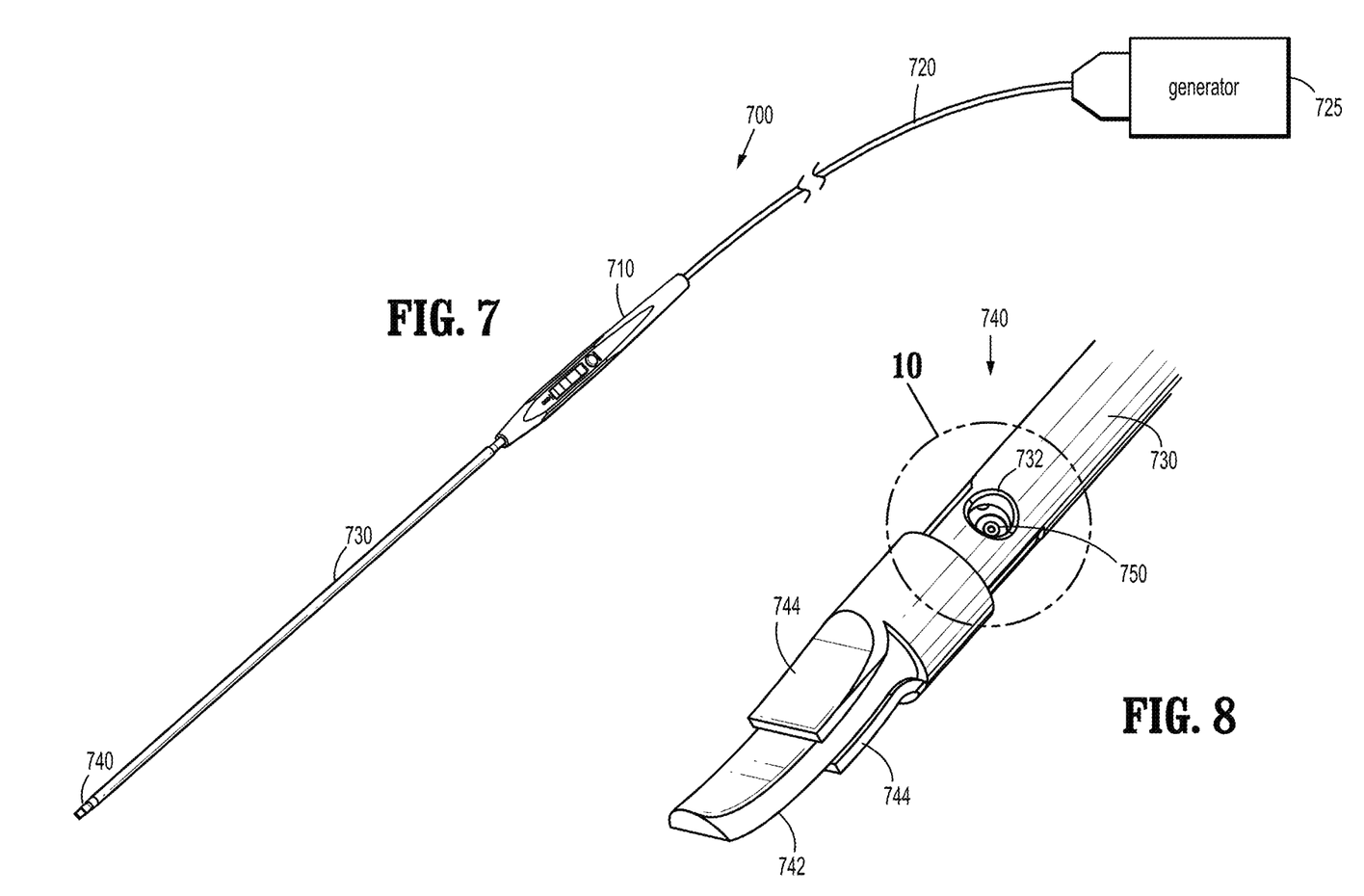
FIG. 7 illustrates a surgical instrument including an electro-cautery cutting element, in accordance with the embodiments of the present disclosure.
FIG. 8 illustrates an enlarged view of the distal end of the surgical instrument including the electro-cautery cutting element of FIG. 7, in accordance with the embodiments of the present disclosure.

FIG. 7 illustrates a surgical instrument 700 including an electro-cautery cutting and sealing element 742, in accordance with the embodiments of the present disclosure, whereas FIG. 8 illustrates an enlarged view of the distal tip 740 of the surgical instrument 700 including the electro-cautery cutting element of FIG. 7, in accordance with the embodiments of the present disclosure.

The surgical instrument 700 may be an electro-cautery knife including a housing 710. One end of the housing 710 is connected to a cable 720, which is connected to a generator 725. The other end of the housing 710 is connected to a shaft 730 having a tip 740. The tip 740 includes an opening 732 within which is housed the receiver 750. The tip further includes a cutting and sealing element 742, such as a knife, secured to the shaft 730 by an insulator 744. The receiver 750 is positioned at a distal end of the surgical instrument 700, the distal end further including the cutting and sealing element 742. In operation, the surgical instrument 700 is used to both dissect tissue and to cauterize blood vessels. Thus, the surgical instrument 700 relies on high-voltage, high-frequency electrical signals of various waveforms to selectively sever, clamp or coagulate living tissue during surgical procedures.

Figure 9:
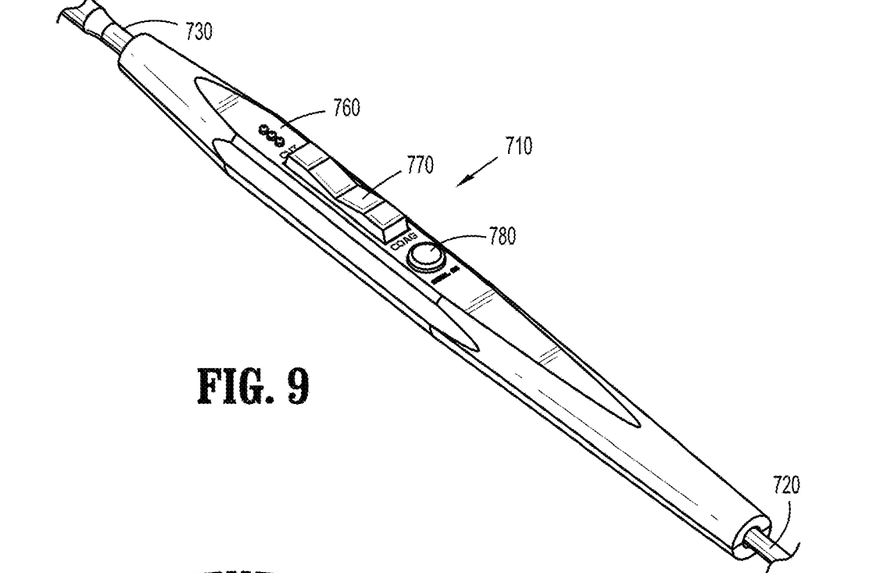
FIG. 9 illustrates an enlarged view of the actuation elements of the surgical instrument including the electro-cautery cutting element of FIG. 7, in accordance with the embodiments of the present disclosure.

FIG. 9 illustrates an enlarged view of the actuation elements of the surgical instrument 700 including the electro-cautery cutting element of FIG. 7, in accordance with the embodiments of the present disclosure.

The housing 710 includes several actuation elements or mechanisms. Actuation mechanism 770 is a rocker type actuator for allowing a user to select between, for example, coagulation and cutting modes. Actuation mechanism 780 activates the "navigation mode," as described below with reference to FIGS. 12 and 13. Indicators 760 may be LED lights indicating whether the tip 740 of the surgical instrument 700 is within a predetermined operating zone 1200, as defined below with reference to FIGS. 12-13. When the tip 740 of the surgical instrument 700 is within the predetermined operating zone 1200, the indicators 760 may turn green, whereas when the tip 740 of the surgical instrument 700 is outside the predetermined operating zone 1200, the indicators 760 may turn red. Of course, it is possible to have further colors, such as yellow and orange, for example, as the tip 740 of the surgical instrument 700 approaches the boundary of the operating zone 1200. Additionally, at least one transmitter of the plurality of transmitters 430 may be triggered when the tip 740 of the surgical instrument 700 approaches or enters the predetermined operating zone 1200.

Figures 10, 11:
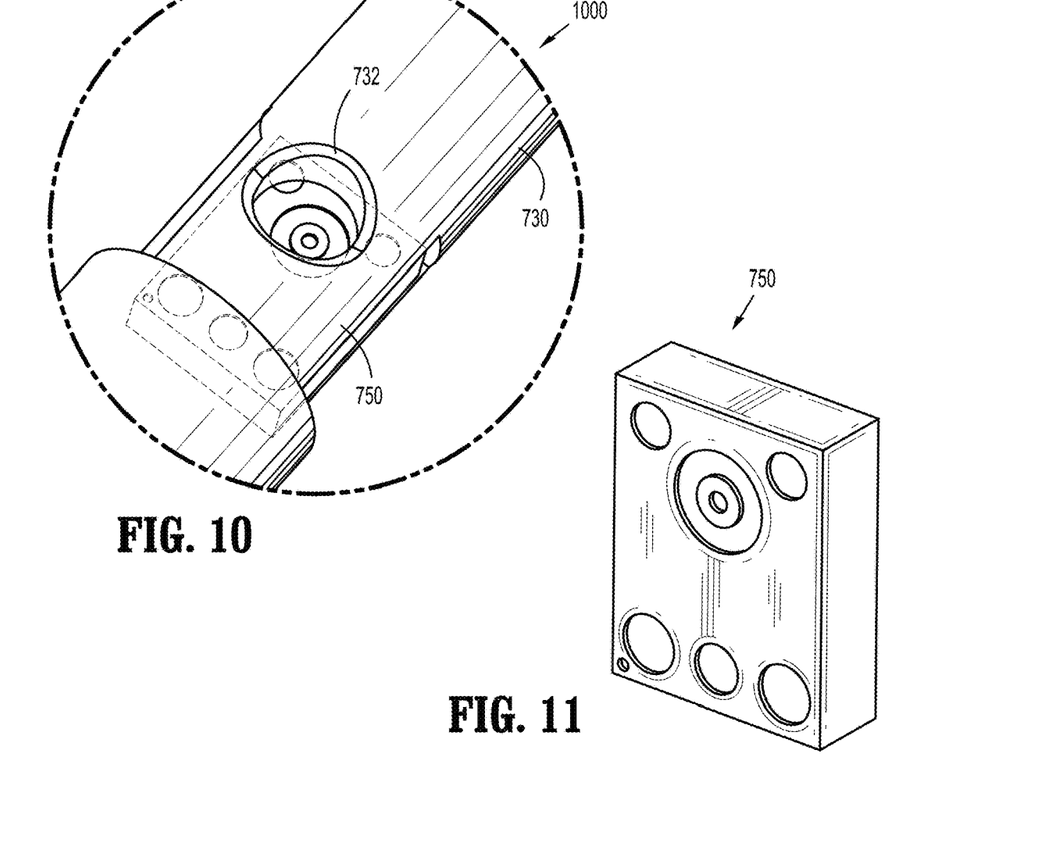
FIG. 10 illustrates the area of detail of FIG. 8 showing an enlarged view of a receiver embedded within the surgical instrument including the electro-cautery cutting element of FIG. 7, in accordance with the embodiments of the present disclosure.
FIG. 11 illustrates the receiver, in accordance with the embodiments of the present disclosure.

FIG. 10 illustrates the area of detail of FIG. 8 showing an enlarged view 1000 of a receiver 750 embedded within the surgical instrument 700 including the electro-cautery cutting element of FIG. 7, in accordance with the embodiments of the present disclosure, whereas FIG. 11 illustrates the receiver 750, in accordance with the embodiments of the present disclosure.

The enlarged view 1000 depicts the receiver 750 resting within the shaft 730 of the surgical instrument 700, such that the receiver 750 is aligned with the opening 732 of the shaft 730. The receiver 750 is configured to communicate with the transmitter 430 of the retaining member 60, as described below with reference to FIGS. 12 and 13.

Figure 12:
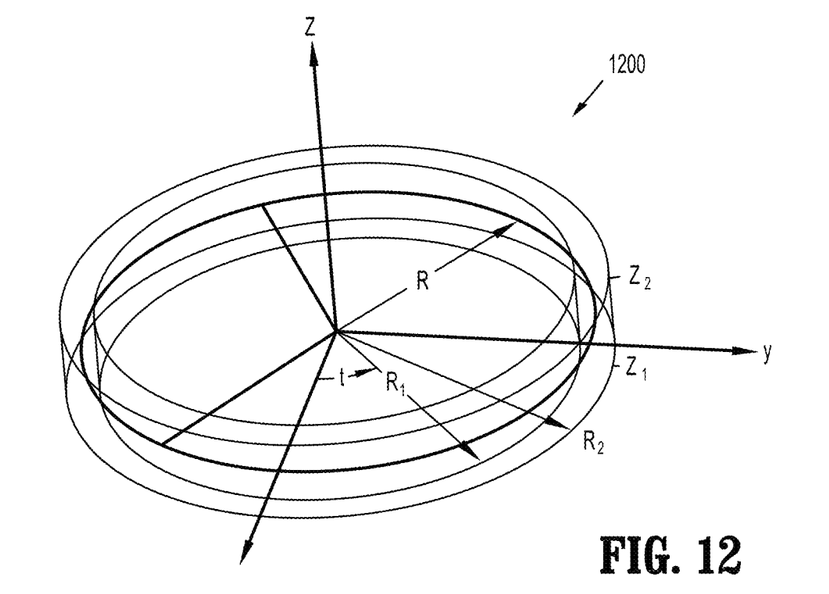
FIG. 12 illustrates a predetermined operating zone of operation of the surgical instrument in cylindrical coordinate system form, in accordance with the embodiments of the present disclosure.
Figure 13:
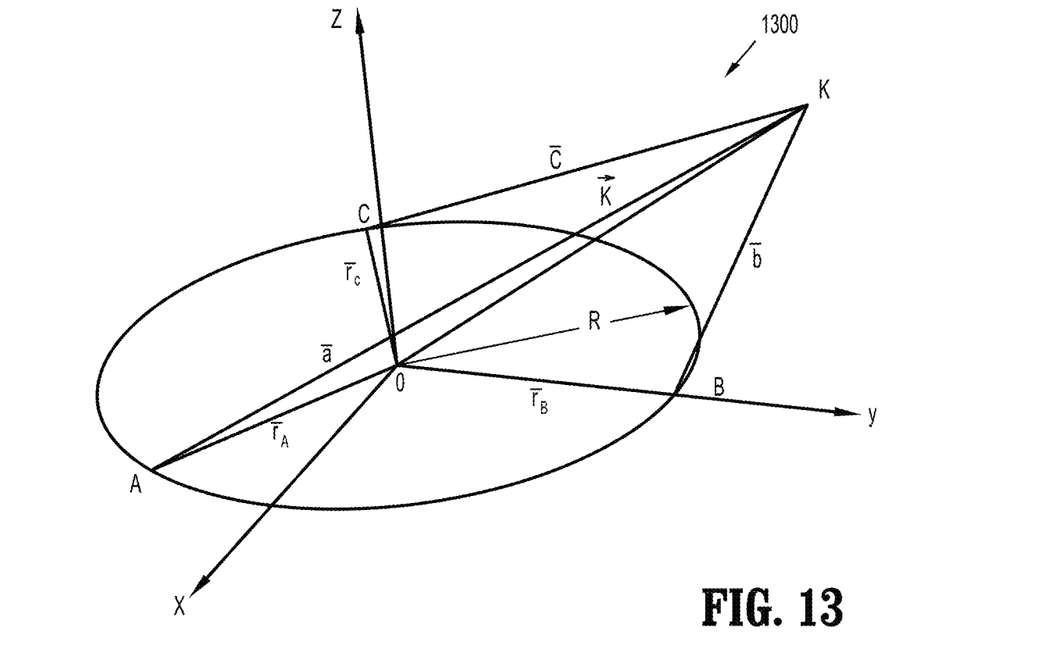
FIG. 13 illustrates, in cylindrical coordinate system form, the electro-cautery cutting element of FIG. 7 being outside the predetermined operating zone of operation, in accordance with the embodiments of the present disclosure.

FIG. 12 illustrates a predetermined operating zone 1200 for the surgical instrument 700 including the electro-cautery cutting and sealing element 742 of FIG. 7, in cylindrical coordinate system form, in accordance with the embodiments of the present disclosure, whereas FIG. 13 illustrates, in cylindrical coordinate system form, the electro-cautery cutting and sealing element 742 of FIG. 7 being in a region 1300 outside the predetermined operating zone 1200, in accordance with the embodiments of the present disclosure. The predetermined operating zone may also be referred to as a safe zone.

Total Laparoscopic Hysterectomy (TLH) is a minimally invasive procedure usually performed for benign indications. The key part of the procedure is the circular transection around the fundus of the cervix, called colpotomy. It separates the uterus from the cervix. It is performed with the surgical instrument 700 including the cutting and sealing element 742, which is inserted to the surgical site through a surgical port. To present the cervical fundus for transection, the surgeon commonly uses the uterine manipulator 100 to reposition/manipulate the uterus.

In operation, and with reference to FIGS. 1 and 2, the uterine manipulator 100 is inserted through the vagina and has a steerable and rotatable first shaft 45 with a first balloon 40 which anchors or secures to the uterus and allows moving it upward, as well as rotating it in a coronal plane. Proximal to the first balloon 40 is the retaining member 60, or colpotomy cup, which rests against the cervical fundus and pushes it up during the surgical procedure. The retaining member 60 serves as a guide during colpotomy. The cervical fundus is located in proximity to several vital organs, including the bladder, color, arteries, urethra, and ureter.

To improve the accuracy of instrument placement during colpotomy, a navigation system is provided. The navigation system determines a distance between the retaining member 60 of the uterine manipulator 100 and the tip 740 of the cutting and sealing element 742 of the surgical instrument 700. Thus, the uterine instrument 100 is operated in tandem with the surgical instrument 700 having the receiver 750 for receiving the at least one signal emitted from the plurality of transmitters 430 of the retaining member 60.

A distance between the cutting and sealing element 742 of the surgical instrument 700 and the distal ring 440 of the retaining member 60 is calculated by a processor (not shown). If the distance exceeds a predetermined threshold, a notification may be relayed to a user of the uterine instrument 100. Alternatively, if the distance exceeds a predetermined threshold, the cutting and sealing element 742 may be automatically deactivated by the processor. In other words, a distance between the cutting and sealing element 742 of the surgical instrument 700 and one end of the retaining member 60 of the uterine instrument 100 is calculated to determine whether the cutting and sealing element 742 is within the predetermined operating zone 1200.

Therefore, the transmitters 430 located on or within the distal ring 440 of the retaining member 60 communicate with the receiver 750 located at the distal end of the surgical instrument 700. Sonic signals may be emitted by the transmitters 430 that are received by the receiver 750. Of course, one skilled in the art may contemplate other types of signals, such as electro-magnetic signals or radio signals. A processor associated with the receiver 750 calculates the distance between each transmitter 430 and the tip 740 having the cutting and sealing element 742 of surgical instrument 700. After calculating such distance, the processor calculates whether the tip 740 having the cutting and sealing element 742 is within the predetermined operating zone 1200 (FIG. 12). This information is then passed on, in real-time, during the surgery, to the surgeon to disable the cutting and sealing element 742 if it is outside the predetermined operating zone 1200.

The predetermined operating zone 1200 is depicted in cylindrical coordinate form in FIG. 12. The predetermined operating zone 1200 may have the shape of a circle or ellipse or toroid or donut or cylinder concentric with the distal ring 440 of the retaining member 60, as shown in FIG. 4. The donut-shaped or cylinder-shaped predetermined operating zone 1200 may have a radius R. If the tip 740 having the knife 742 is in the predetermined operating zone 1200, then the following conditions are satisfied:

$$R_1 \leq R_K \leq R_2$$

$$z_1 \leq z_K \leq z_2$$

for: $0° \leq t \leq 360°$ where $R_K$, $z_K$, t are the coordinates of the cutting tip K of the electro-cautery instrument in the cylindrical coordinate system, and where $R_1$, $R_2$, $z_1$, $z_2$ are the limits of the allowable donut shape zone around the colpotomy cup ring (r=R, z=0) where a safe transaction can be performed.

In other words, the knife 742 is within the confines or boundaries or within the radius R of the donut-shaped or cylinder-shaped predetermined operating zone 1200. Of course, one skilled in the art may contemplate any width or height for the predetermined operating zone 1200.

Regarding FIG. 13, it is assumed that the transmitters 430 are located at points A, B, and C of the distal ring 440 represented in cylindrical coordinate system form and defined by the vectors $R_A$, $R_B$, and $R_C$. Each transmitter 430 transmits a signal in sequence which travels with specific speed through tissue and reaches the receiver 750. The receiver 750 receives those signals transmitted by the transmitters 430 and based on measured travel time calculates the distances a, b, and c from the respective transmitters 430 to the receiver 750. Now the processor solves a set of equations to find the Cartesian coordinates of vectors a, b, and c, and then the coordinates of vector K ($x_K$, $y_K$, $z_K$), where vector K extends from O to K (FIG. 13) and K represents the tip 740 of the cutting element 742. Since $R_K = SQRT(x_K^2 + y_K^2)$, the processor can now check whether the tip 740 having the cutting element 742 is within the predetermined operating zone 1200 for performing the colpotomy.

Thus, the navigation system provided herein allows the activation of the surgical instrument 700 only when the tip 740 having the cutting element 742 is within the predetermined operating zone 1200 or in close proximity to the outer boundary or outer perimeter or edge of the retaining member 60. Therefore, the surgeon can perform colpotomy safely while avoiding contact with adjacent tissue. In other words, the cutting element 742 must operate within the confines or boundary or outer perimeter of the distal ring 440 of the retaining member 60. If the cutting element 742 falls outside the boundary of the distal ring 440 of the retaining element 60, then the cutting element 742 is deactivated either automatically or by the surgeon.

Figure 14:
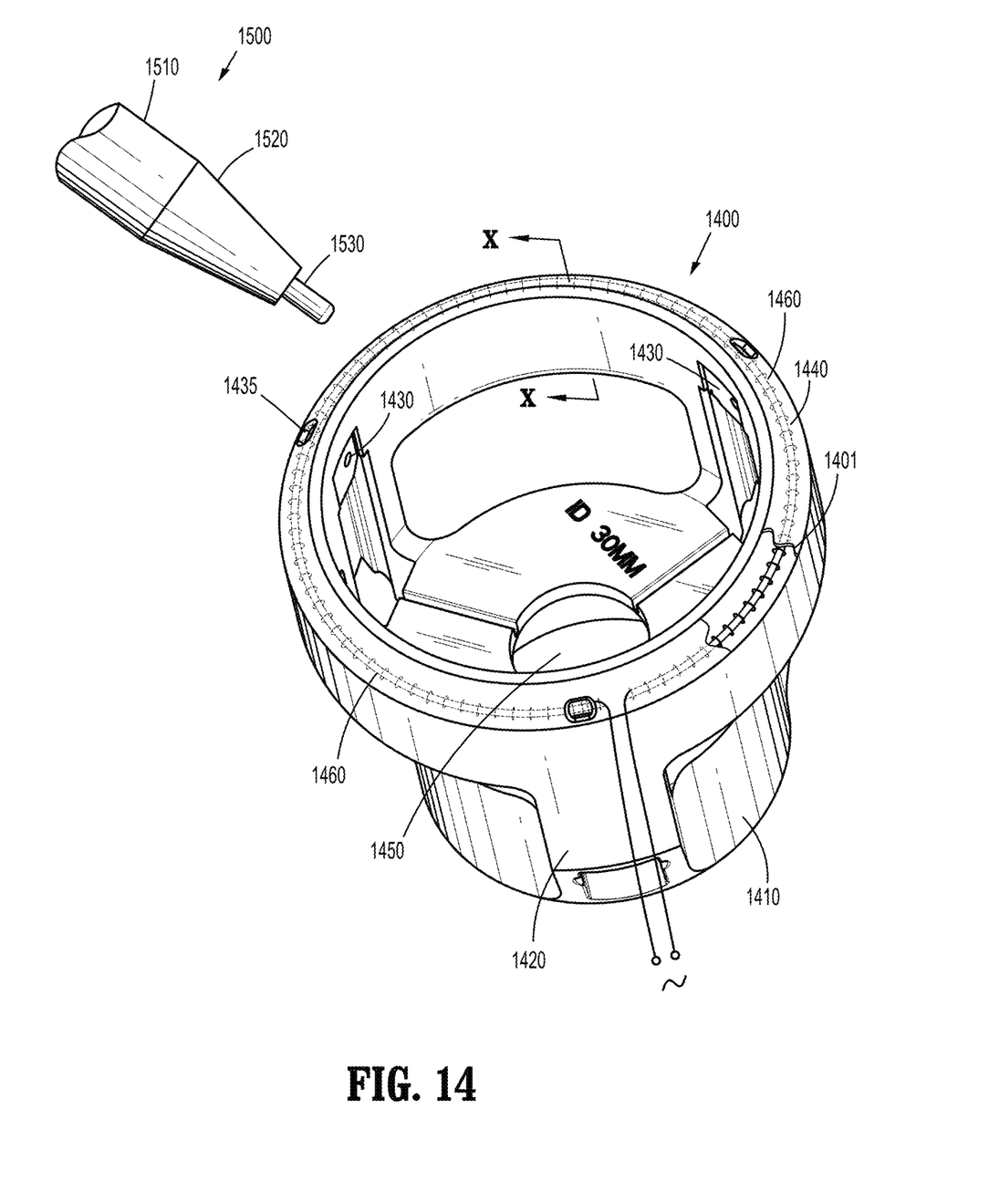
FIG. 14 illustrates a retaining member incorporating a single inductive coil loop, as well as a tip of a surgical cutting device approaching a distal ring of the retaining member, in accordance with another embodiment of the present disclosure.

FIG. 14 illustrates a retaining member 1400 incorporating a single inductive coil loop 1460, as well as a tip 1530 of a surgical cutting device 1500 approaching a distal ring 1440 of the retaining member 1400, in accordance with another embodiment of the present disclosure.

The retaining member 1400 includes a proximal ring 1410 and a distal ring 1440. The proximal ring 1410 has a plurality of posts 1420 for supporting the distal ring 1440. In one exemplary embodiment, there are three posts 1420. Alternatively, the proximal ring 1410 may be a solid ring with no posts.

The retaining member 1400 further includes a central opening 1450 for receiving a shaft 1510 of the surgical cutting device 1500. The surgical cutting device 1500 further includes a tapered portion 1520 and a tip 1530 extending from the tapered portion 1520. The tapered portion 1520 may be constructed from a ferromagnetic material. The ferromagnetic material may preferably be a metal. The tip 1530 may be an electrocautery isolated tip.

The distal ring 1440 includes a plurality of transmitters 1430. In the exemplary embodiments there are, for example, 3 transmitters 1430 embedded or incorporated within the distal ring 1440. Each transmitter 1430 may be aligned with a post 1420. Each transmitter 1430 may emit a single frequency sound wave through a respective opening 1435. Of course, one skilled in the art may contemplate the transmitters 1430 transmitting other types of signals, such as electromagnetic signals or radio signals. The transmitters 1430 may emit the same frequency or each transmitter 1430 may emit a unique frequency. One skilled in the art may contemplate any number of transmitters embedded within different portions of the distal ring 1440.

A single inductive coil loop 1460 is incorporated or embedded within the distal ring 1440 of the retaining member 1400. A cutout section 1401 depicts a portion of the single inductive coil loop 1460 circumferentially embedded or incorporated within the retaining member 1400.

Figure 15:
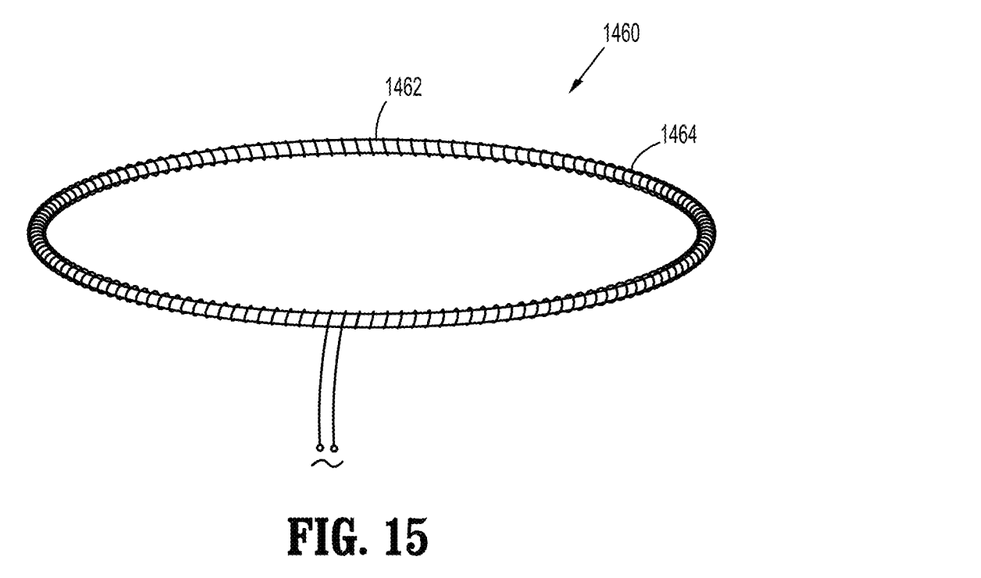
FIG. 15 illustrates the single inductive coil loop used in the retaining member of FIG. 14, in accordance with embodiments of the present disclosure.

FIG. 15 illustrates the single inductive coil loop 1460 used in the retaining member 1400 of FIG. 14, in accordance with embodiments of the present disclosure.

The single inductive coil loop 1460 includes a core 1462 and a wire 1464 wound around the entire length of the core 1462.

Figure 16:
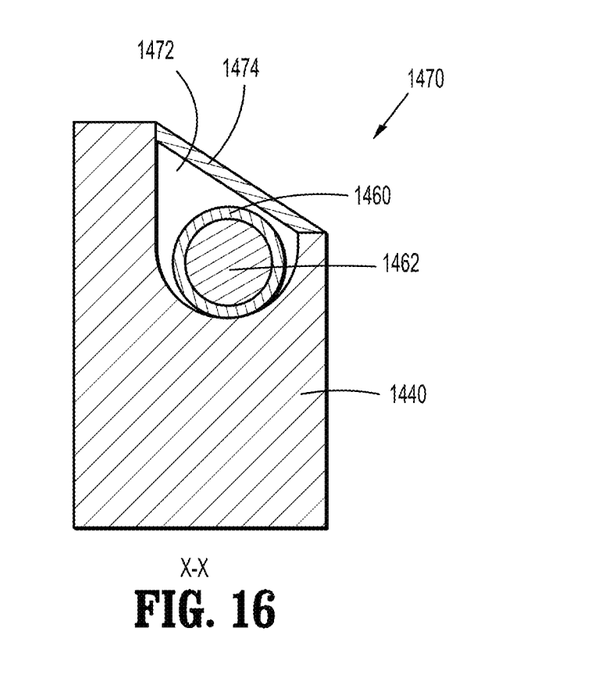
FIG. 16 illustrates a cross-sectional view of the distal ring of the retaining member taken along line X-X of FIG. 14, in accordance with embodiments of the present disclosure.

FIG. 16 illustrates a cross-sectional view 1470 of the distal ring 1440 of the retaining member 1400 taken along line X-X of FIG. 14, in accordance with embodiments of the present disclosure.

The distal ring 1440 defines an opening 1472 for accommodating the single inductive coil loop 1460 therein. A cover 1474 encloses the single inductive coil loop 1460 within the distal ring 1440. The cover 1474 may serve as an isolator. The opening 1472 may be a substantially semi-circular opening.

Figure 19:
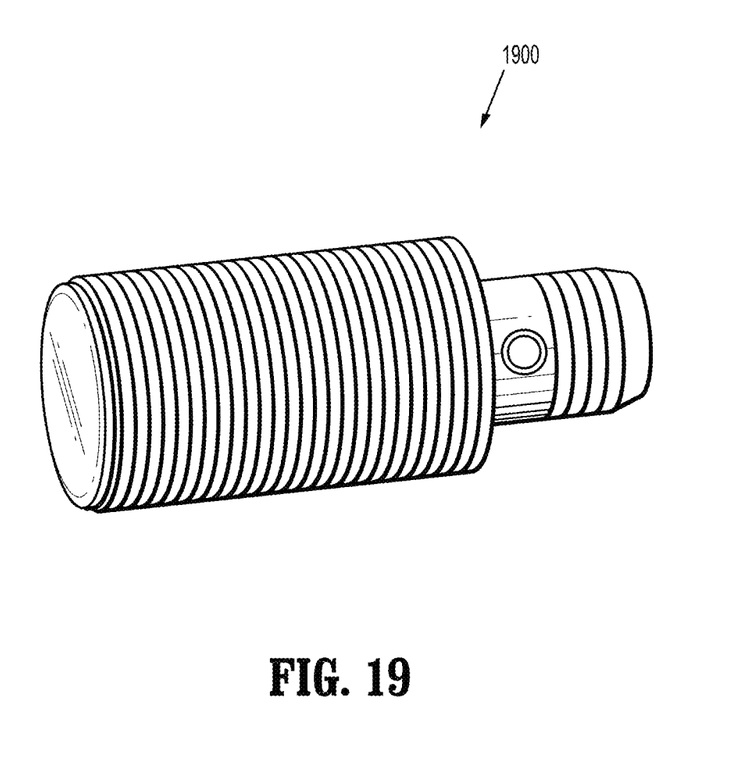
FIG. 19 illustrates an inductive sensor that serves as the inductive coil loops used in FIGS. 14 and 17, in accordance with embodiments of the present disclosure.

Referring to FIGS. 14-16, the single inductive coil loop 1460 allows for a method of sensing a radial position of the tip 1530 of the surgical cutting device 1500, as the tip 1530 approaches the distal ring 1440 of the retaining member 1400. The single inductive coil loop 1460 serves as an inductive sensor (FIG. 19). The tip 1530 of the surgical cutting device 1500 includes a tapered portion 1520 composed or formed or constructed from a ferromagnetic material. The ferromagnetic material may preferably be a metal. Once the tip 1530 is in close proximity to the retaining member 1400, the tapered portion 1520 changes the inductance of the single inductive coil loop 1460. This data or information is transmitted by the transmitters 1430 to, for example, a display device. A user can evaluate or analyze the data or information collected and, based on that data or information, safely conduct transection of the uterus without risk of damaging adjacent organs. Such data or information is valuable when visibility of the operating site is impaired.

Figure 17:
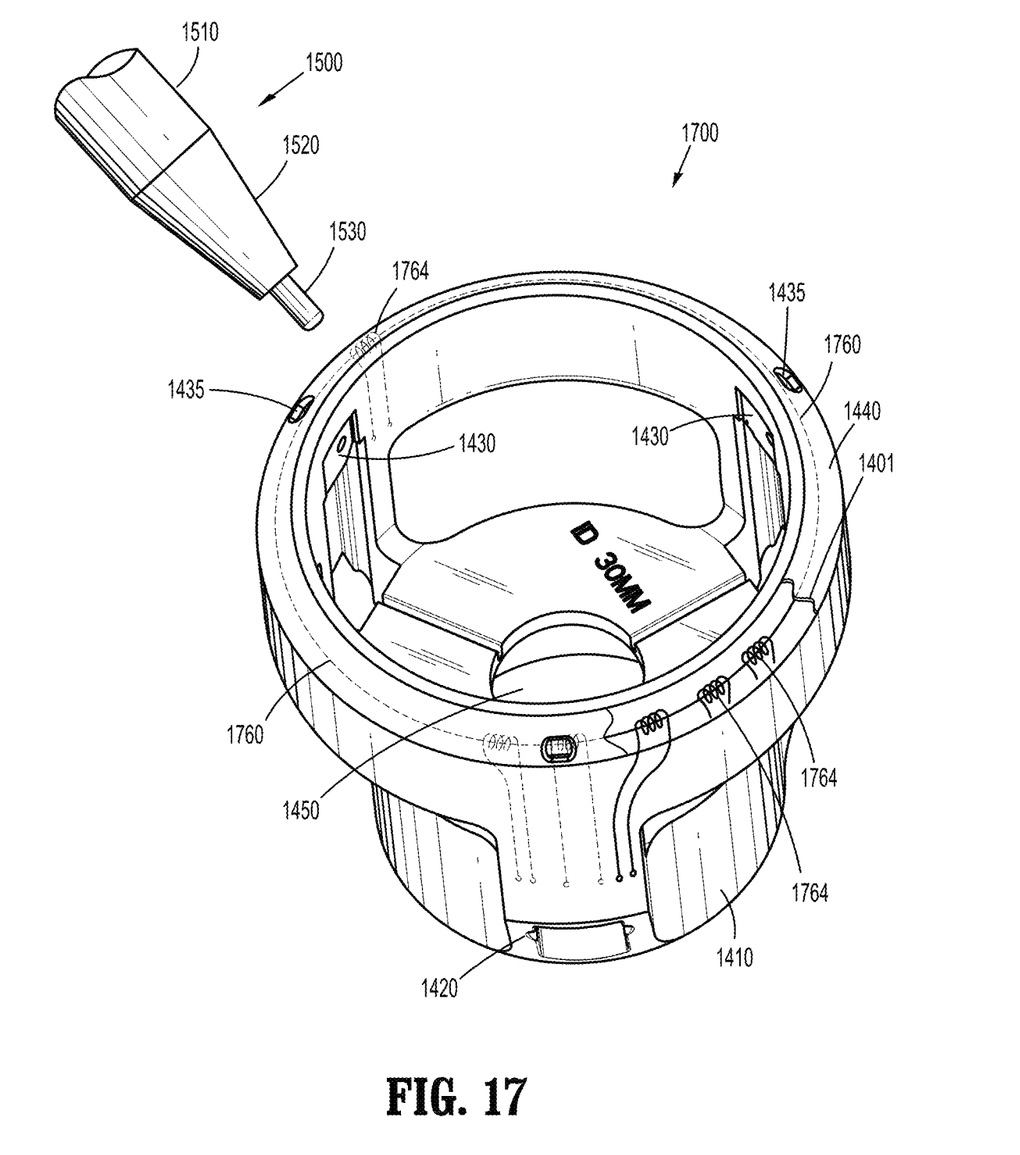
FIG. 17 illustrates a retaining member incorporating a series of inductive coil loops, as well as a tip of a surgical cutting device approaching a distal ring of the retaining member, in accordance with another embodiment of the present disclosure.

FIG. 17 illustrates a retaining member 1700 incorporating a series of inductive coil loops 1764, as well as a tip 1530 of a surgical cutting device 1500 approaching a distal ring 1440 of the retaining member 1700, in accordance with another embodiment of the present disclosure.

The retaining member 1700 includes a proximal ring 1410 and a distal ring 1440. The proximal ring 1410 has a plurality of posts 1420 for supporting the distal ring 1440. In one exemplary embodiment, there are three posts 1420. Alternatively, the proximal ring 1410 may be a solid ring with no posts.

The retaining member 1700 further includes a central opening 1450 for receiving a shaft 1510 of the surgical cutting device 1500. The surgical cutting device 1500 further includes a tapered portion 1520 and a tip 1530 extending from the tapered portion 1520. The tapered portion 1520 may be constructed from a ferromagnetic material. The ferromagnetic material may preferably be a metal. The tip 1530 may be an electrocautery isolated tip.

The distal ring 1440 includes a plurality of transmitters 1430. In the exemplary embodiments there are 3 transmitters 1430 embedded or incorporated within the distal ring 1440. Each transmitter 1430 may be aligned with a post 1420. Each transmitter 1430 may emit a single frequency sound wave through a respective opening 1435. Of course, one skilled in the art may contemplate the transmitters 1430 transmitting other types of signals, such as electromagnetic signals or radio signals. The transmitters 1430 may emit the same frequency or each transmitter 1430 may emit a unique frequency. One skilled in the art may contemplate any number of transmitters embedded within different portions of the distal ring 1440.

A series of inductive coil loops 1764 are incorporated or embedded within the distal ring 1440 of the retaining member 1700 via a core 1760. A cutout section 1401 depicts a portion of the series of inductive coil loops 1764 circumferentially embedded or incorporated within the retaining member 1700. The series of inductive coil loops 1764 are positioned around a core 1760. The series of inductive coil loops 1764 may be equally spaced apart from each other around the core 1760.

Figure 18:
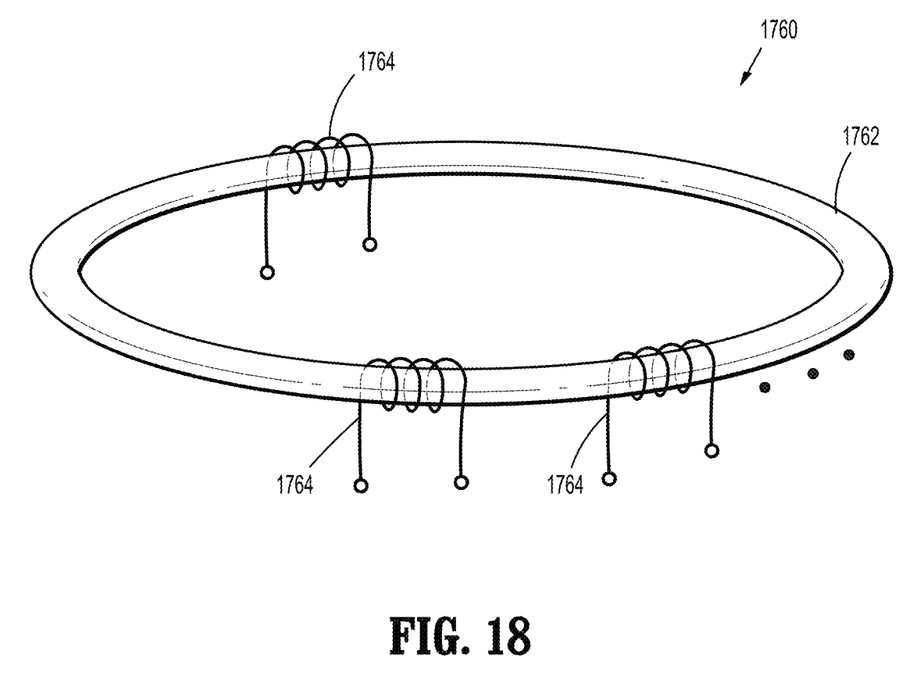
FIG. 18 illustrates the series of inductive coil loops used in the retaining member of FIG. 17, in accordance with embodiments of the present disclosure.

FIG. 18 illustrates the series of inductive coil loops 1764 used in the retaining member 1700 of FIG. 17, in accordance with embodiments of the present disclosure.

The series of inductive coil loops 1764 are wires that are placed or positioned around the core 1760. One skilled in the art may contemplate any number of inductive coil loops 1764 wound around the core 1762.

Referring to FIGS. 17-18, the series of inductive coil loops 1764 allow for a method of sensing a radial position, as well as an angular position of the tip 1530 of the surgical cutting device 1500, as the tip 1530 approaches the distal ring 1440 of the retaining member 1700. Each of the inductive coil loops 1764 serves as an inductive sensor (FIG. 19). The tip 1530 of the surgical cutting device 1500 includes a tapered portion 1520 composed or formed or constructed from a ferromagnetic material. The ferromagnetic material may preferably be a metal. Once the tip 1530 is in close proximity to the retaining member 1700, the tapered portion 1520 changes the inductance of the series of inductive coil loops 1764. This data or information is transmitted by the transmitters 1430 to, for example, a display device. A user can evaluate or analyze the data or information collected and, based on that data or information, safely conduct transection of the uterus without risk of damaging adjacent organs. Such data or information is valuable when visibility of the operating site is impaired.

FIG. 19 illustrates an inductive sensor 1900 that serves as the inductive coil loops used in FIGS. 14 and 17, in accordance with embodiments of the present disclosure. In FIG. 14, one single coil served as an inductive sensor to identify a radial location of a tip of an instrument, whereas in FIG. 17, a series of coils constituted a series of inductive sensors allowing identification of both radial and angular location of the tip of the surgical instrument. The inductive sensor is an electronic proximity sensor, which detects metallic objects without touching them. The sensor consists of an induction loop, as illustrated in FIGS. 15 and 18.

It is to be understood that the various embodiments shown and described herein are to be taken as exemplary. Elements and materials, and arrangements of those elements and materials, may be substituted for those illustrated and described herein, parts may be reversed, and certain features of the present disclosure may be utilized independently, all as would be apparent to one skilled in the art after having the benefit of the description herein. Changes may be made in the elements described herein without departing from the spirit and scope of the present disclosure and following claims, including their equivalents. It is to be understood that the particular examples and embodiments set forth herein are non-limiting, and modifications to structure, dimensions, materials, and methodologies may be made without departing from the scope of the present disclosure.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed:

1. A uterine instrument comprising:
   a first handle portion;
   a second handle portion;
   a first shaft operably coupled to the first handle portion, the first shaft having a first balloon positioned at a distal end thereof;
   a second shaft operably coupled to the second handle portion, the second shaft having a second balloon positioned at a distal end thereof;
   a retaining member configured to engage the second balloon of the second shaft, the retaining member including a distal ring, the first shaft configured to extend through the second shaft and the retaining member to access a surgical site; and
   a plurality of transmitters disposed about the distal ring of the retaining member, wherein each transmitter of the plurality of transmitters transmits at least one signal, including a single frequency sound wave, radially inward to define a predetermined operating zone.

2. The uterine instrument of claim 1, wherein the first handle portion is a movable handle and the second handle portion is a stationary handle.

3. The uterine instrument of claim 1, wherein, in operation, the first balloon is inflated to retain the first shaft in a uterus and the second balloon is inflated to seal an abdominal cavity.

4. The uterine instrument of claim 1, wherein the retaining member is a colpotomy cup.

5. The uterine instrument of claim 1, wherein the retaining member further includes a proximal ring, the proximal ring having a plurality of posts for supporting the distal ring.

6. The uterine instrument of claim 1, wherein the uterine instrument is operated in tandem with a surgical instrument having at least one receiver for receiving the at least one signal emitted from the plurality of transmitters.

7. The uterine instrument of claim 6, wherein the at least one receiver is positioned at a distal end of the surgical instrument, the distal end further including a cutting element.

8. The uterine instrument of claim 7, wherein a distance between the cutting element of the surgical instrument and the distal ring of the retaining member is calculated by a processor.

9. The uterine instrument of claim 8, wherein if the distance exceeds a predetermined threshold, a notification is relayed to a user of the uterine instrument.

10. The uterine instrument of claim 8, wherein if the distance exceeds a predetermined threshold, the cutting element is automatically deactivated.

11. A colpotomy system comprising:
    a surgical instrument having a cutting element and a receiver at a distal end thereof; and
    a uterine instrument having a handle operably coupled to a shaft having a balloon at a distal end thereof, the shaft extending through a retaining member to access a surgical site, the retaining member including a plurality of transmitters, wherein each transmitter of the plurality of transmitters transmits at least one signal, including a single frequency sound wave, radially inward to define a predetermined operating zone;
    wherein a distance between the cutting element of the surgical instrument and one end of the retaining member of the uterine instrument is calculated to determine whether the cutting element is within the predetermined operating zone.

12. The colpotomy system according to claim 11, wherein the retaining member has a proximal ring and a distal ring, the proximal ring having a plurality of posts for supporting the distal ring.

13. The colpotomy system according to claim 12, wherein a transmitter of the plurality of transmitters is incorporated within the distal ring.

14. The colpotomy system of claim 12, wherein the predetermined operating zone is defined by the circumference of the distal ring.

15. The colpotomy system of claim 11, wherein if the distance exceeds a predetermined threshold, a notification is relayed to a user of the uterine instrument.

16. The colpotomy system of claim 11, wherein if the distance exceeds a predetermined threshold, the cutting element is automatically deactivated.

17. A method of accessing a surgical site, the method comprising:
    introducing at the surgical site a surgical instrument having a cutting element and a receiver at a distal end thereof;
    introducing at the surgical site a uterine instrument having a handle operably coupled to a shaft having a balloon at a distal end thereof, the shaft extending through a retaining member to access the surgical site, the retaining member including a plurality of transmitters, wherein each transmitter of the plurality of transmitters transmits at least one signal, including a single frequency sound wave, radially inward to define a predetermined operating zone;
    calculating a distance between the cutting element of the surgical instrument and one end of the retaining member of the uterine instrument; and
    determining whether the cutting element is within the predetermined operating zone.

* * * * *